United States Patent
Peters et al.

(10) Patent No.: US 11,495,351 B2
(45) Date of Patent: Nov. 8, 2022

(54) HEALTH MONITORING SYSTEM AND METHOD THEREOF

(71) Applicant: Robert Bosch GmbH, Stuttgart (DE)

(72) Inventors: Christian Peters, Sunnyvale, CA (US); Seow Yuen Yee, Mountain View, CA (US); Thomas Rocznik, Mountain View, CA (US); Fabian Henrici, Sunnyvale, CA (US)

(73) Assignee: Robert Bosch GmbH, Stuttgart (DE)

( * ) Notice: Subject to any disclaimer, the term of this patent is extended or adjusted under 35 U.S.C. 154(b) by 295 days.

(21) Appl. No.: 16/609,713

(22) PCT Filed: Aug. 28, 2018

(86) PCT No.: PCT/EP2018/073069
§ 371 (c)(1),
(2) Date: Oct. 30, 2019

(87) PCT Pub. No.: WO2019/042957
PCT Pub. Date: Mar. 7, 2019

(65) Prior Publication Data
US 2020/0066404 A1    Feb. 27, 2020

Related U.S. Application Data

(60) Provisional application No. 62/552,915, filed on Aug. 31, 2017.

(51) Int. Cl.
*A61B 5/00* (2006.01)
*G16H 40/67* (2018.01)

(52) U.S. Cl.
CPC .......... *G16H 40/67* (2018.01); *A61B 5/0015* (2013.01); *A61B 2560/0223* (2013.01)

(58) Field of Classification Search
CPC .......... A61B 2560/0223; A61B 5/0015; G16H 20/30; G16H 40/67
See application file for complete search history.

(56) References Cited

U.S. PATENT DOCUMENTS

| 2004/0077958 | A1 | 4/2004 | Hiroyuki et al. |
| 2011/0125040 | A1 | 5/2011 | Crawford et al. |
| 2013/0165800 | A1 | 6/2013 | Shimizu et al. |

(Continued)

OTHER PUBLICATIONS

International Search Report corresponding to PCT Application No. PCT/EP2018/073069, dated Dec. 4, 2018 (4 pages).

*Primary Examiner* — George Manuel
(74) *Attorney, Agent, or Firm* — Maginot, Moore & Beck LLP

(57) ABSTRACT

A method of calibrating a monitoring device to generate calibrated vital sign data using a calibration device includes positioning the monitoring device in a first position on a patient, generating vital sign data with a sensing assembly of the positioned monitoring device, and processing the vital sign data with the calibration device to determine if the vital sign data is calibrated vital sign data or uncalibrated vital sign data. The method also includes generating a calibrated data signal if the vital sign data is calibrated vital sign data, generating a reposition signal if the vital sign data is uncalibrated vital sign data, and repositioning the monitoring device on the patient until the calibrated data signal is generated.

13 Claims, 14 Drawing Sheets

(56) References Cited

U.S. PATENT DOCUMENTS

2014/0303524 A1* 10/2014 Chen ................... A61B 5/11
600/595
2017/0215016 A1* 7/2017 Dohmen .............. H04R 1/1091

* cited by examiner

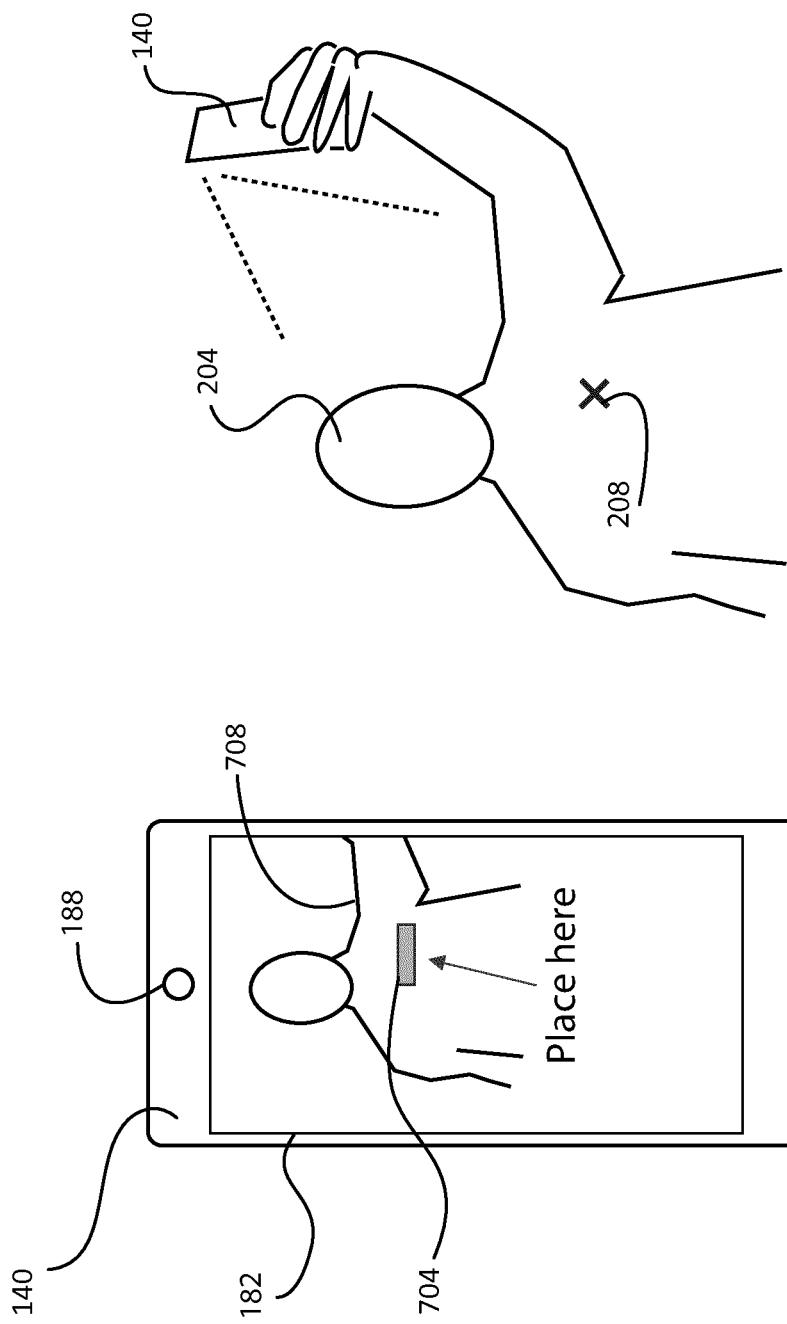

HEALTH MONITORING SYSTEM AND METHOD THEREOF

This application is a 35 U.S.C. § 371 National Stage Application of PCT/EP2018/073069 filed on Aug. 28, 2018, which claims the benefit of priority of U.S. provisional application Ser. No. 62/552,915, filed on Aug. 31, 2017, the disclosures of which are incorporated herein by reference in their entirety.

FIELD

This disclosure is related to health monitoring systems and, more particularly, to an autonomous electronic assistant device of a health monitoring system.

BACKGROUND

Health monitoring systems enable health care providers to remotely monitor a patient's vital signs, for example. An exemplary health monitoring system monitors a patient's heart rate with a corresponding sensor and transmits electronic data of the heart rate to a remote server. In this way, the health care provider can monitor the patient's vital signs while the patient is located in the comfort of her own home.

During remote monitoring, the patient may desire to remove and reposition the sensor or another portion of the health monitoring system as may occur when the patient bathes or when the sensor become depleted of electrical energy. During repositioning, the patient may position the sensor at a location that results in an inaccurate reading, an uncalibrated reading, or no reading at all. In such a situation, the health care provider is prevented from monitoring the patient's vital signs. Accordingly, further developments for health monitoring systems are desired to assist patients and healthcare providers in the positioning of a health monitoring system for generating accurate readings of a patient's vital signs.

SUMMARY

A summary of certain embodiments disclosed herein is set forth below. It should be understood that these aspects are presented merely to provide the reader with a brief summary of these certain embodiments and that these aspects are not intended to limit the scope of this disclosure. This disclosure may encompass a variety of aspects that may not be set forth below.

Embodiments of the disclosure are related to an autonomous electronic assistant for a health monitoring system.

According to an exemplary embodiment, a method is disclosed of calibrating a monitoring device to generate calibrated vital sign data using a calibration device. The method includes positioning the monitoring device in a first position on a patient, generating vital sign data with a sensing assembly of the positioned monitoring device, and processing the vital sign data with the calibration device to determine if the vital sign data is calibrated vital sign data or uncalibrated vital sign data. The method also includes generating a calibrated data signal if the vital sign data is calibrated vital sign data, generating a reposition signal if the vital sign data is uncalibrated vital sign data, and repositioning the monitoring device on the patient until the calibrated data signal is generated.

According to another exemplary embodiment of the disclosure a health monitoring system includes a monitoring device and a calibration device. The monitoring device includes a sensing assembly configured to generate vital sign data of a patient. The calibration device is operably connected to the monitoring device and includes a processor configured to calibrate the monitoring device by generating a calibrated data signal if the vital sign data is calibrated vital sign data, and generating a reposition signal if the vital sign data is uncalibrated vital sign data. The monitoring device is configured to be moved on the patient from a first position to a second position in response to the calibration device generating the reposition signal.

BRIEF DESCRIPTION OF THE DRAWINGS

These and other features, aspects, and advantages of this disclosure will become better understood when the following detailed description of certain exemplary embodiments is read with reference to the accompanying drawings in which like characters represent like arts throughout the drawings, wherein:

FIG. 13 illustrates simplified schematic diagram of a calibration device configured as a smartphone for use with the health monitoring system, as disclosed herein;

FIG. 14 illustrates the patient using the calibration device of FIG. 13 to assist in positioning the monitoring device of the health monitoring system relative to a monitoring zone.

DETAILED DESCRIPTION

One or more specific embodiments will be described below. It should be appreciated that in the development of any actual implementation, as in any engineering or design project, numerous implementation-specific decisions must be made to achieve the developer's specific goals, such as compliance with system-related and business-related constraints, which may vary from one implementation to another. Moreover, it should be appreciated that such development effort might be complex and time consuming, but would nevertheless be a routine undertaking of design, fabrication, and manufacturing for those of ordinary skill having the benefit of this disclosure.

The following description is presented to enable any person skilled in the art to make and use the described embodiments, and is provided in the context of a particular application and its requirements. Various modifications to the described embodiments will be readily apparent to those skilled in the art, and the general principles defined herein may be applied to other embodiments and applications without departing from the spirit and scope of the described embodiments. Thus, the described embodiments are not limited to the embodiments shown, but are to be accorded the widest scope consistent with the principles and features disclosed herein.

Figure 1:
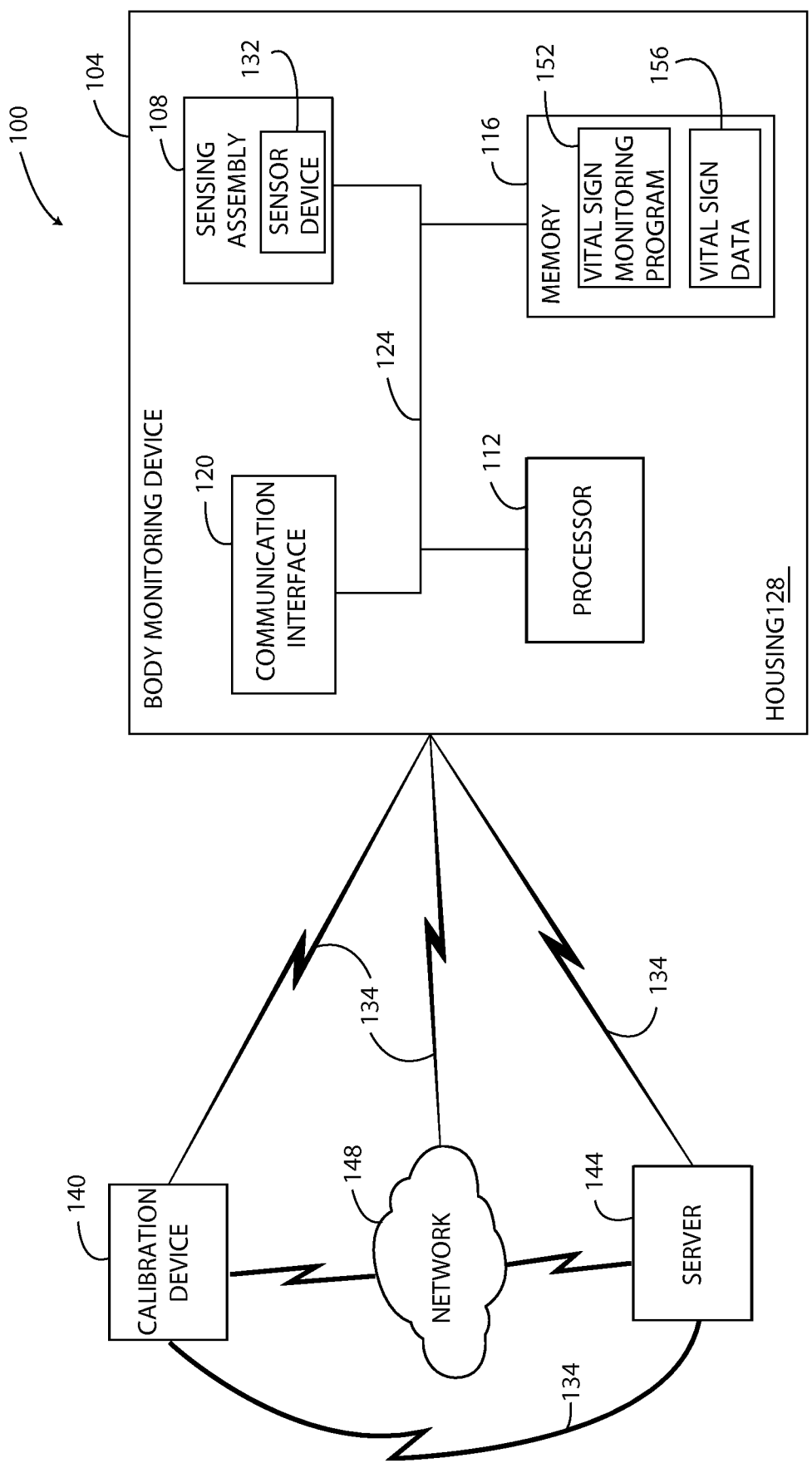
FIG. 1 illustrates a block diagram of a health monitoring system, as disclosed herein, including a body monitoring device and a calibration device.

FIG. 1 illustrates an exemplary embodiment of a health monitoring system 100 including a body monitoring device 104, a calibration device 140, a server 144, and a network 148. The body monitoring device 104, also referred to herein as a monitoring device, is configured to monitor a vital sign or signs of a patient 204 (FIG. 4, for example) including cardiac activity, body temperature, pulse (i.e. heart rate), blood pressure, respiratory rate, and so forth. As used herein, the term "patient" includes all people and all users of the system 100 including users that are sick or ill and people that have no illness or no sickness. The calibration device 140 is configured to assist a user in calibrating and/or positioning the monitoring device 104 on a specific region of the patient 204. The calibration device 140 enables a user or the patient to position the monitoring device 104 to have an optimized signal strength, to generate optimized data, and/or to generate calibrated data. Each component of the health monitoring system 100 is described herein.

The body monitoring device 104 may be removably worn by the patient 204, applied to the body, skin, or clothing of the patient 204, or placed near the patient 204 on a bedside table, for example. The monitoring device 104 is configured as a patch, a neckless, a chest strap, a pendant, or any other device that locates the monitoring device 104 in a position suitable for monitoring a desired vital sign or signs of the patient 204. The monitoring device 104 may be a patch-like device applied on any location of the patient's body. For example, the monitoring device 104 is configured as a blood pressure patch and/or a heart rate patch. In another embodiment, the monitoring device 104 is implanted into the patient 204, such that the monitoring device 104 may be configured as a pacemaker, for example.

The monitoring device 104, as shown in FIG. 1, includes a sensing assembly 108, a processor 112, a memory 116, and a communication interface 120 each communicatively coupled to each other via a bus 124. An optional energy source (not shown) may be coupled to or integrated into the monitoring device 104 to power or energize the monitoring device 104. The energy source may be a battery or an energy harvesting device. The energy source may be charged and recharged with a wireless charging device (not shown) such as a Qi charger, a wireless power transfer device, an inductive charging device, or any other suitable charging device.

The monitoring device 104 further includes a housing 128 that, in at least some embodiments, is configured to encapsulate at least one or more of the sensing assembly 108, the processor 112, the memory 116, and the communication interface 120. In one embodiment, the housing 128 is a thin-film material, configured as a patch, that stretches, bends, twists, folds, expands, contracts, or any combination thereof in response to movement of the patient 204 to which the monitoring device 104 is applied. Moreover, when the housing 128 is configured as a patch, the monitoring device 104 may be worn by, applied to, reapplied to, removed from, positioned, or repositioned at a monitoring site 208 (FIG. 4) of the patient 204. An exemplary monitoring site 208 is the sternum 216 (FIG. 4) of the patient 204 or is a predetermined distance 220 (FIG. 4) from the sternum 216. Typically, the housing 128 is configured for direct contact with the skin of the patient 204 and includes an adhesive to removably mount the monitoring device 104 to the skin of the patient 204.

With continued reference to FIG. 1, the memory 116 of the monitoring device 104 is communicatively coupled to the processor 112 and is configured to store computer-readable instructions and programs that, when executed by the processor 112, cause the monitoring device 104, and more particularly the processor 112, to monitor the vital signs and/or the cardiac activity of the patient 204 based on an output of the sensing assembly 108. For example, the memory 116 includes a vital signs monitoring program 152 for monitoring the vital signs of the patient 204 using the sensing assembly 108 by causing the sensing assembly 108 to generate vital sign data 156 of the patient 204 corresponding to the monitored vital sign(s). The vital sign data 156 is stored in the memory 116. The memory 116 may include any transitory, non-transitory, volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

The processor 112 is configured as a microprocessor ($\mu$P), a microcontroller ($\mu$C), a digital signal processor (DSP), a central processing unit (CPU), a graphical processing unit (GPU), or any combination thereof. In one embodiment, the processor 112 includes one or more levels of caching, such as a level cache memory, one or more processor cores, and registers. The example processor cores may (each) include an arithmetic logic unit (ALU), a floating point unit (FPU), a digital signal processing core (DSP Core), or any combination thereof. The processor 112 may also be operatively connected to or include a memory controller (not shown).

The communication interface 120, shown in FIG. 1, configures the monitoring device 104 for bidirectional transmission of data with an external device (such as the calibration device 140), the server 144, and/or the network 148. Specifically, the monitoring device 104 may communicate directly with the external device or indirectly with the external device via the server 144 and the network 148 (i.e. the Internet). The communication interface 120 transmits and receives data in the form of signals or data packets which may be, for example, electronic, electromagnetic, or optical. The communication interface 120 may be a modem, a network interface, a communication port, a PCM-CIA slot and card, or the like. The communication interfere 120 is operable with standards such as Bluetooth, Zigbee, Thread, IEEE802.15.4, WiFi, Near-Field Communication (NFC), Z-wave, or any other suitable wireless protocol capable to transmit/receive data between devices and/or systems. Other forms of establishing a communication link using the communication interface 120 include radio-frequency identification (RFID), bar code, and QR code. The communication interface 120 may also be configured as a reader or an imaging sensor such as a camera built-in to the monitoring device (see FIG. 12). Moreover, in some embodiments, a separate reader or a camera (not shown) is operably connected to the monitoring device 104 via the communication interface 120.

With reference to FIG. 1, the sensing assembly 108 is configured to detect at least one or more health or vital signals of the patient 204 and to generate corresponding vital sign data 156 that is stored in the memory 116. Exemplary vital signals monitored by the sensing assembly 108 include electrocardiogram (ECG) signals, motion signals, photoplethysmorgram (PPG) signals, seismocardiogram signals (SCG), ballistocardiogram (BCG) signals, cardiac activity of the patient 204, body temperature, pulse (i.e. heart rate), blood pressure, respiratory rate, combinations thereof, and/or any other vital sign of the patient. Depending on the embodiment, more than one motion signal or vital sign may be detected/monitored by the sensing assembly 108.

The sensing assembly 108 includes at least one sensor device 132. The sensor device 132 may be an accelerometer, a motion sensor, an optical sensor, a transducer, a Doppler ultrasonic transducer, an acoustic sensor, an electrode, an ECG sensor, a patient orientation sensor, a sonar sensor, a thermal sensor, an environmental sensor, a heart rate sensor, and/or any suitable sensor or transducer. The data generated by the sensor device 132 corresponds to the vital sign data 156.

In one embodiment, the sensing assembly 108 is a single-axis sensing assembly. In another embodiment, the sensing assembly 108 is a double-axis sensing assembly. In yet another embodiment, the sensing assembly 108 is a multi-axis assembly. As an example, a first sensor device 132 is located at a first axis of the patient 204 for detecting a first time-dependent motion waveform representative of one or more contractile properties of the patient's heart and a second sensor device 132 is located at a second axis of the patient 204 for detecting a second time dependent motion waveform representative of the patient's blood flow. The sensing assembly 108 may include additional sensor devices 132 provided at locations along any axis or axes of the patient 204 to either remove motion artifacts (as a reference sensor) or detect attributes from the environment for providing context awareness information to the health monitoring system 100.

The monitoring device 104 may be a wired computing system or a wireless computing system. In one embodiment, the monitoring device 104 is (or is operably connected to) a cloud computing device (such as the server 144) which may be communicated with via the Internet over the network 148, and which may be co-located or geographically distributed, such that shared resources and/or a computer program are provided to computers and other devices on demand for example, as will be appreciated by those skilled in the art. The computer program may be stored on a memory (not shown) of the server 144. The computer program, also known as a program, software, software application, script, application or code, can be written in any form of programming language, including compiled or interpreted languages, declarative or procedural languages, and it can be deployed in any form, including a standalone program or as a module, component, subroutine, object, or other unit suitable for use in a computing environment. The computer program may, but need not, correspond to a file in a file system. The computer program can be stored in a portion of a file that holds other computer programs or data (e.g. one or more scripts stored in a markup language document), in a single file dedicated to the program in question, or in multiple coordinated files. In another embodiment, the monitoring device 104 configured for cloud computing is implemented as one or more servers which may be communicated with via the Internet.

The monitoring device 104 may communicatively couple to the calibration device 140, the server 144, and/or the network 148 via one or more links 134. The links 134 may be wired, wireless, or combination thereof. The wireless communication link 134 may include cellular protocol, data packet protocol, radio frequency protocol, satellite band, optical communication protocols including infrared channel, or any other protocol able to transmit data among client machines. The wired communication link 134 may include any wired line link.

The server 144 is communicatively coupled to the calibration device 140, the body monitoring device 104, and the network 148. The server 144 may be an application server, a certificate server, a mobile information server, an e-commerce server, a FTP server, a directory server, CMS server, a printer server, a management server, a mail server, a public/private access server, a real-time communication server, a database server, a proxy server, a streaming media server, a cloud server, or the like.

The network 148, in one embodiment, comprises one or more sub-networks, and can be installed between any combination of the calibration device 140 and the server 144. In some embodiments, the network 148 can be, for example, the Internet, a local-area network (LAN), a metropolitan area network (MAN), a wide area network (WAN), a primary network comprised of multiple sub-networks located between the calibration device 140 and the server 144, or a cloud network. Further embodiments of the network 148 include a point-to-point network, a broadcast network, a telecommunication network, a data communication network, a computer network, an ATM (Asynchronous Transfer Mode) network, a SONET (Synchronous Optical Network) network, a SDH (Synchronous Digital Hierarchy) network, a wireless network, a wireline network, and the like. Depending on the application, other networks may be used so that data exchanged between the calibration device 140 and the server 144 can be transmitted over the network 148. Network topology of the network 148 can differ within different embodiments which may include a bus network topology, a star network topology, a ring network topology, a repeater-based network topology, or a tiered-star network topology. Additional embodiments may include a network 148 of mobile telephone networks that use a protocol to communicate among mobile devices, where the protocol can be for example AMPS, TDMA, CDMA, GSM, GPRS, UMTS, LTE or any other protocol able to transmit data among mobile devices.

Figure 2:
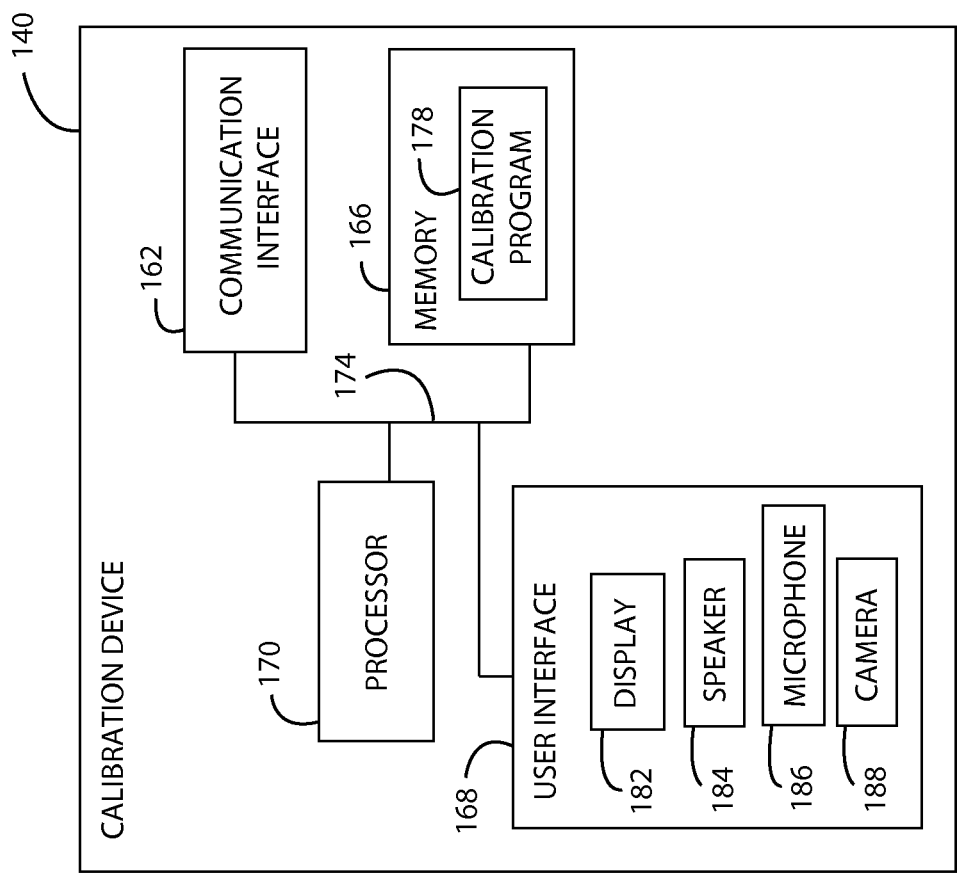
FIG. 2 illustrates a block diagram of the calibration device of FIG. 1.

As shown in FIG. 2, the calibration device 140 is operably connected to the monitoring device 104 and is configured to facilitate an intelligent calibration/positioning of the monitoring device 104 relative to the patient 204. The calibration device 140 which may also be referred to herein as a computing device, a client device, and/or an external device, may be a personal computer or desktop computer, a laptop, a cellular or smartphone, a tablet, a personal digital assistant (PDA), a phablet, a gaming console, an audio device, a video device, an entertainment device such as a television, a vehicle infotainment, a wearable device, a thin client system, a thick client system, a home appliance, a smart home assistant, a voice-controlled assistant, or the like. The calibration device 140 can, in some embodiments, be referred to as a single computing device or a single group of computing devices, while the server 144 may be referred to as a single server or a single group of servers. In one embodiment a single calibration device 140 communicates with more than one server 144, while in another embodiment a single server 144 communicates with more than one calibration device 140. In yet another embodiment, a single calibration device 140 communicates with a single server 144.

The calibration device 140 includes a communication interface 162, a memory 166, and a user interface 168 operatively connected to a processor 170 via a bus 174. The communication interface 162 configures the calibration device 140 for bidirectional transmission of data with the monitoring device 104. The calibration device 140 may communicate directly with the monitoring device 104 or indirectly with the monitoring device 104 via the server 144 and the network 148. The communication interface 162 transmits and receives data in the form of signals or data packets which may be, for example, electronic, electromagnetic, or optical. The communication interface 162 may be for example a modem, a network interface, a communication port, a PCM-CIA slot and card, or the like. The communication interfere 162 is operable with standards such as Bluetooth, Zigbee, Thread, IEEE802.15.4, WiFi, Near-Field Communication (NFC), Z-wave, or any other suitable wireless protocol capable to transmit/receive data between devices and/or systems. Other forms of establishing a communication link using the communication interface 162 include radio-frequency identification (RFID), bar code, and QR code. The communication interface 162 may also be configured as a reader or an imaging sensor such as a camera built-in to the calibration device. Moreover, in some embodiments, a separate reader or a camera is operably connected to the calibration device via the communication interface.

With continued reference to FIG. 2, the memory 166 of the calibration device 140 is communicatively coupled to the processor 170 and is configured to store computer-readable instructions and programs that, when executed by the processor 170, cause the calibration device 140, and more particularly the processor 170, to calibrate the monitoring device 104. For example, the memory 166 includes an autonomous calibration program 178 for calibrating the monitoring device 104 to accurately sense a desired vital sign or vital signs of the patient 204. The memory 166 may include any transitory, non-transitory, volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

The user interface 168 of the calibration device 140, in one embodiment, includes a display screen 182, a speaker 184, a microphone 186, and a camera 188. The display screen 182 is configured to display information to a user of the health monitoring system 100. The display screen 182 may display text, numbers, and picture information including video information. In another embodiment, the display screen 182 is configured as a series of LEDs having a corresponding label such as "Move the monitoring device away from the patient's sternum," and "Move the monitoring device toward the patient's sternum," for example. The speaker 184 (i.e. audio transducer) is configured to output audible information to the user of the health monitoring system 100. The microphone 186 is configured to receive voice inputs from the user. The camera 188 maybe a front or rear facing camera configured to generate image data for display on the display screen 182. In some embodiments, the user interface 168 also includes tactile input devices, such as a switch, button, or a series of switches and/or buttons. In further embodiments, the calibration device 140 does not include the user interface 168 and a user interface for the health monitoring system 100 is included on an external device.

The processor 170 of the calibration device 140 is configured as a microprocessor (µP), a microcontroller (µC), a digital signal processor (DSP), a central processing unit (CPU), a graphical processing unit (GPU), or any combination thereof. In one embodiment, the processor 170 includes one or more levels of caching, such as a level cache memory, one or more processor cores, and registers. The example processor cores may (each) include an arithmetic logic unit (ALU), a floating point unit (FPU), a digital signal processing core (DSP Core), or any combination thereof. The processor 112 may also be operatively connected to or include a memory controller (not shown).

Figure 3:
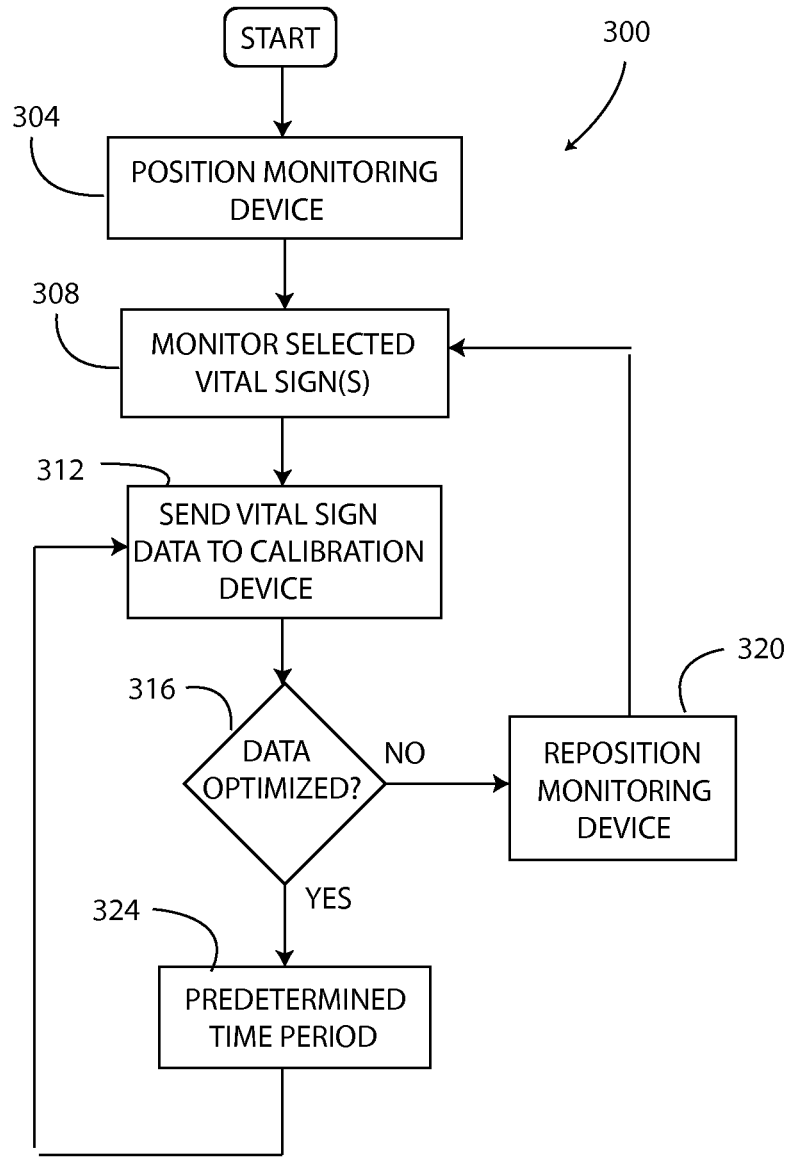
FIG. 3 is a flowchart illustrating a method of operating the health monitoring system of FIG. 1.
Figure 4:
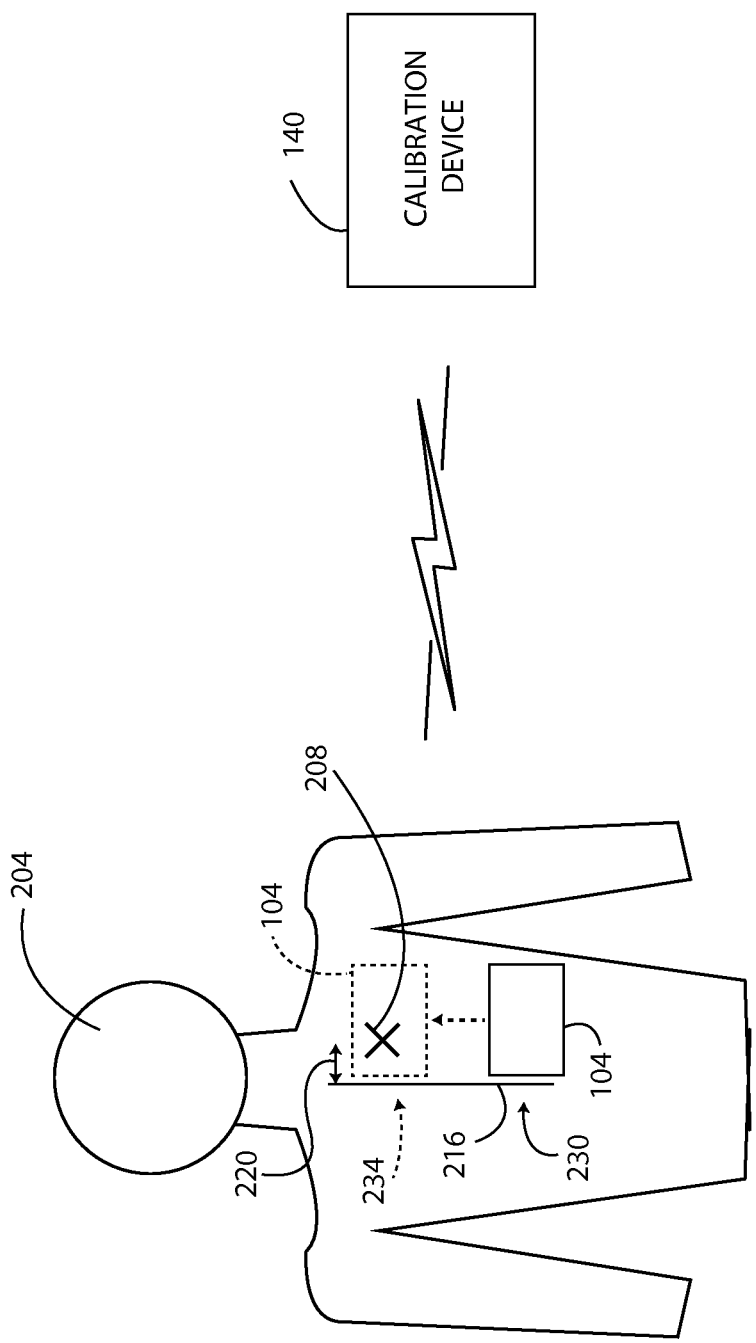
FIG. 4 is a block diagram of a patient and the health monitoring system of FIG. 1, and illustrates a repositioning of the monitoring device to optimize and to calibrate the data generated by the monitoring device according to the method of FIG. 3.

In operation and with reference to FIGS. 3 and 4, the health monitoring system 100 is configured to implement a method 300 of calibrating the monitoring device 104 using the processor 170 and the autonomous calibration program 178 of the calibration device 140. In block 304, to calibrate the monitoring device 104 to generate calibrated vital sign data 156, first the user places the monitoring device 104 on a region of the patient that is thought to be close to the monitoring site 208 and may be referred to herein as a first position or an initial location 230. The specific location of the monitoring site 208 varies from person to person based on the patient's unique physiology. Thus, while a general location of the monitoring site 208 may be known, the exact location of the monitoring site 208 that produces optimized vital sign data, calibrated vital sign data, and/or vital sign data having a strong signal strength is typically unknown. In this example, the person placing the monitoring device 104 may be the patient 204, a healthcare professional, or another person assisting the patient 204. The monitoring device 104 is located within communication range of the calibration device 140, such that the link 134 is established between the monitoring device 104 and the calibration device 140. The link 134 may be wired or wireless.

As shown in the example of FIG. 4, the solid line rendering of the monitoring device 104 represents an initial placement 230 of the monitoring device 104 in the first position and the broken line rendering of the monitoring device 104 is a repositioned location 234 of the monitoring device 104 (according to the method 300) in a second position. At the initial location 230, the monitoring device 104 is spaced apart from the monitoring site 208, such that no portion of the monitoring device 104 is located at the monitoring site 208. At the repositioned location 234, the monitoring device 104 covers or at least covers partially the monitoring site 208.

Next, in block 308, the monitoring device 104 is activated and begins to execute the monitoring program 152 to generate the vital sign data 156 with the sensing assembly 108. In one embodiment, the monitoring device 104 activated by the patient 204 or the healthcare provider. In another embodiment, the monitoring device 104 is activated remotely via the link 134 to the network 148, for example. In a further embodiment, the monitoring device 104 automatically starts to generate the vital sign data 156 after the monitoring device 104 is attached to the patient 204. The vital sign data 156 are stored to the memory 116.

In an exemplary embodiment, when the monitoring device 104 is in the initial location 230, the monitoring device 104 does not generate meaningful vital sign data 156. That, is the vital sign data 156 is not representative of the desired vital sign to be monitored, the vital sign data 156 is inaccurate, the vital sign data 156 is uncalibrated, and/or the vital sign data 156 has a low signal strength.

In block 312, the method 300 includes transmitting the vital sign data 156 generated by the monitoring device 104 to the calibration device 140. The vital sign data 156 is transmitted via the link 134 by either a wired or a wireless communication standard.

With reference to block 316, the method 300 includes processing the vital sign data 156 received by the calibration device 140 to determine if the monitoring device 104 is located in an optimized location on or near the monitoring site 208. Specifically, the calibration device 140 calibrates the position of the monitoring device 104 on the patient 204 relative to the monitoring site 208 by processing the vital sign data 156 to determine if the vital sign data 156 is optimized. That is, the calibration device 140 calibrates the position of the monitoring device 104 on the patient 204 relative to the monitoring site 208 by processing the vital sign data 156 to determine if the vital sign data 156 is calibrated vital sign data or uncalibrated vital sign data. The calibration device 140 may use the network 148 to transmit the vital sign data 156 to a remote processing device (such as the server 144) that is configured to process the vital sign data 156.

In one embodiment, using the calibration program 178, the calibration device 140 processes the vital sign data 156 to determine if the vital sign data 156 corresponds to expected vital sign data 156 or calibrated vital sign data. For example, if the monitoring device 104 is configured to monitor blood pressure, the calibration device 140 compares a systolic pressure determined from the vital sign data 156 to a known systolic pressure readings. The calibration device 140 determines that the vital sign data 156 is optimized or calibrated when the systolic pressure from the vital sign data 156 is inside of an expected systolic pressure range. And the calibration device 140 determines that the vital sign data 156 is not optimized or uncalibrated when the systolic pressure from the vital sign data 156 is outside of the expected systolic pressure range. Moreover, if the calibration device 140 cannot determine a systolic pressure from the vital sign data 156 then the calibration device 140 determines that the vital sign data 156 is not optimized or is uncalibrated. The vital sign data 156 may not include the desired vital sign information when the monitoring device 104 is placed too far from a monitoring zone 208, for example. The calibration device 140 generates a calibrated data signal if it is determined that the vital sign data 156 is calibrated vital sign data or are optimized data. The calibration device 140 generates a reposition signal if it is determined that the vital sign data 156 is uncalibrated vital sign data or are un-optimized data.

In another embodiment, the monitoring device 104 is configured to monitor the heart rate of the patient 204. In such an embodiment, the processor 170 of the calibration device 140 runs the calibration program 178 to determine if the vital sign data 156 corresponding to the patient's heart rate is optimized. The calibration device 140 determines that the vital sign data 156 is optimized when the heart rate determined from the vital sign data 156 is inside of an expected heart rate range (i.e. a data range). And the calibration device 140 determines that the vital sign data 156 is not optimized when the heart rate from the vital sign data 156 is outside of the expected heart rate range. Moreover, if the calibration device 140 cannot determine a heart rate from the vital sign data 156 then the calibration device 140 determines that the vital sign data 156 is not optimized.

In another embodiment, the monitoring device 104 is configured to monitor any other vital sign of the patient 204. In such an embodiment, the processor 170 of the calibration device 140 runs the calibration program 178 to determine if the vital sign data 156 corresponding to the vital sign is optimized by evaluating a signal strength of the vital sign data 156. The calibration device 140 determines that the vital sign data 156 is optimized when the signal strength (or a signal to noise ratio "SNR") of the vital sign data 156 is inside of an expected signal strength range or above a signal strength threshold. And the calibration device 140 determines that the vital sign data 156 is not optimized when the signal strength of the vital sign data 156 is outside of the expected signal strength range or below the signal strength threshold. Moreover, if the calibration device 140 cannot determine a signal strength from the vital sign data 156 then the calibration device 140 determines that the vital sign data 156 is not optimized.

Further in block 316 of the method 300, the calibration device 140 has used the calibration program 178 to determine that the vital sign data 156 generated by the monitoring device 104 is not optimized. Accordingly, the calibration device 140 generates a reposition signal by activating the user interface 168 to generate a human perceptible alert to indicate that the position of the monitoring device 104 should be adjusted. The alert generated by the user interface 168 may be a visual alert from the display screen 182 or an audible alert from the speaker 184 and is referred to herein as the reposition signal. Specifically, in one embodiment, the calibration device 140 generates a tone that increases in volume the closer that the monitoring device 104 is to the monitoring zone 208. In another embodiment, the calibration device 140 emits an audible or visual message stating, "Move the monitoring device toward the patient's sternum," or "Move the monitoring device away from the patient's sternum," to assist in repositioning the monitoring device 104 to generate the optimized vital sign data 156. In a further embodiment, the calibration device 140 generates the reposition signal as visual instructions on the display screen 182 indicating how the monitoring device 104 should be repositioned to generate the optimized vital sign data 156. Such an embodiment, is described with in detail in connection with FIGS. 13 and 14.

Next, in block 320 of the method 300, the monitoring device 104 is repositioned relative to the monitoring zone 208 in response to the reposition signal. As shown in FIG. 4, the monitoring device 104 is moved from the initial location 230 to the repositioned location 234 so that the monitoring device is located over the monitoring zone of the particular patient. Depending on the level of detail in the reposition signal generated by the calibration device 140, the user moving the monitoring device 104 may or may not know if the monitoring device 104 has been moved to the monitoring zone 230. The movement of the monitoring device 104 may be a trial and error process that is repeated numerous times.

After repositioning the monitoring device 104 in the repositioned location 234, in block 308 of the method 300, the monitoring device 104 generates the vital sign data 156 again. Then, in block 312 of the method 300, the vital sign data 156 is sent to the calibration device 140. In block 316, the calibration device 140 processes the vital sign data 156 from the repositioned monitoring unit 104 to determine if the vital sign data 156 is optimized.

Since the monitoring device 104 in the repositioned location 234 is located over the monitoring zone 208, the monitoring device 104 generates optimized vital sign data 156. However, the user or the patient may not know the precise location of the monitoring zone 208 and, thus, the calibration device 140 is used to confirm that the monitoring device 104 is positioned in an acceptable location. In one embodiment, the calibration device 140 generates the calibrated data signal to indicate that the monitoring device 104 is positioned properly and that the vital sign data 156 is calibrated vital sign data. The calibrated data signal is a human perceptible signal that may be visual or audible and typically is generated by the user interface 168.

In block 324 of the method 300, after determining that the vital sign data 156 generated by the monitoring device 104 is optimized, the calibration device 140 allows a predetermined time period to elapse. The predetermined time period ranges from one minute to one hour or longer.

Next, after the predetermined time period, the calibration device 140 causes the monitoring device 104 to send again the vital sign data 156 to ensure that the vital sign data 156 is still optimized. The method 300 continuous to periodically check the vital sign data 156 for optimization because the monitoring device 104 may be moved away from the monitoring zone 208 (intentionally or unintentionally) or the monitoring device 104 may become depleted of electrical energy. If at any point during the collection of the vital sign data 156 by the monitoring device 104, the calibration device 140 determines that the vital sign data 156 is no longer optimized, the calibration device 140 generates the reposition signal to alert the patient 204 or a caretaker that the monitoring device 104 should be repositioned closer to the monitored zone 208 to calibrate the data and/or to improve the signal strength.

In another embodiment, at block 324 instead of starting the predetermined time period, the method 300 ends and the monitoring device 104 generates and stores the vital sign data 156.

Based on the above method 300, the health monitoring system 100 is configured to simplify the placement of the monitoring device 104 on the patient 204. If the monitoring device 104 is not positioned properly, perhaps due to the unique physiology of the patient 204, then the calibration device 140 determines that the vital sign data 156 is not optimized and will alert the patient 204 or the caretaker accordingly. In one embodiment, the monitoring device 104 is "hovered" over the patient 204 until the calibration device 140 emits a tone or stops emitting a tone to alert the user that the monitoring device 104 positioned properly. In addition, the optimized position can change over time as the system 100 can learn through previous measurements and adapt accordingly.

Figure 5:
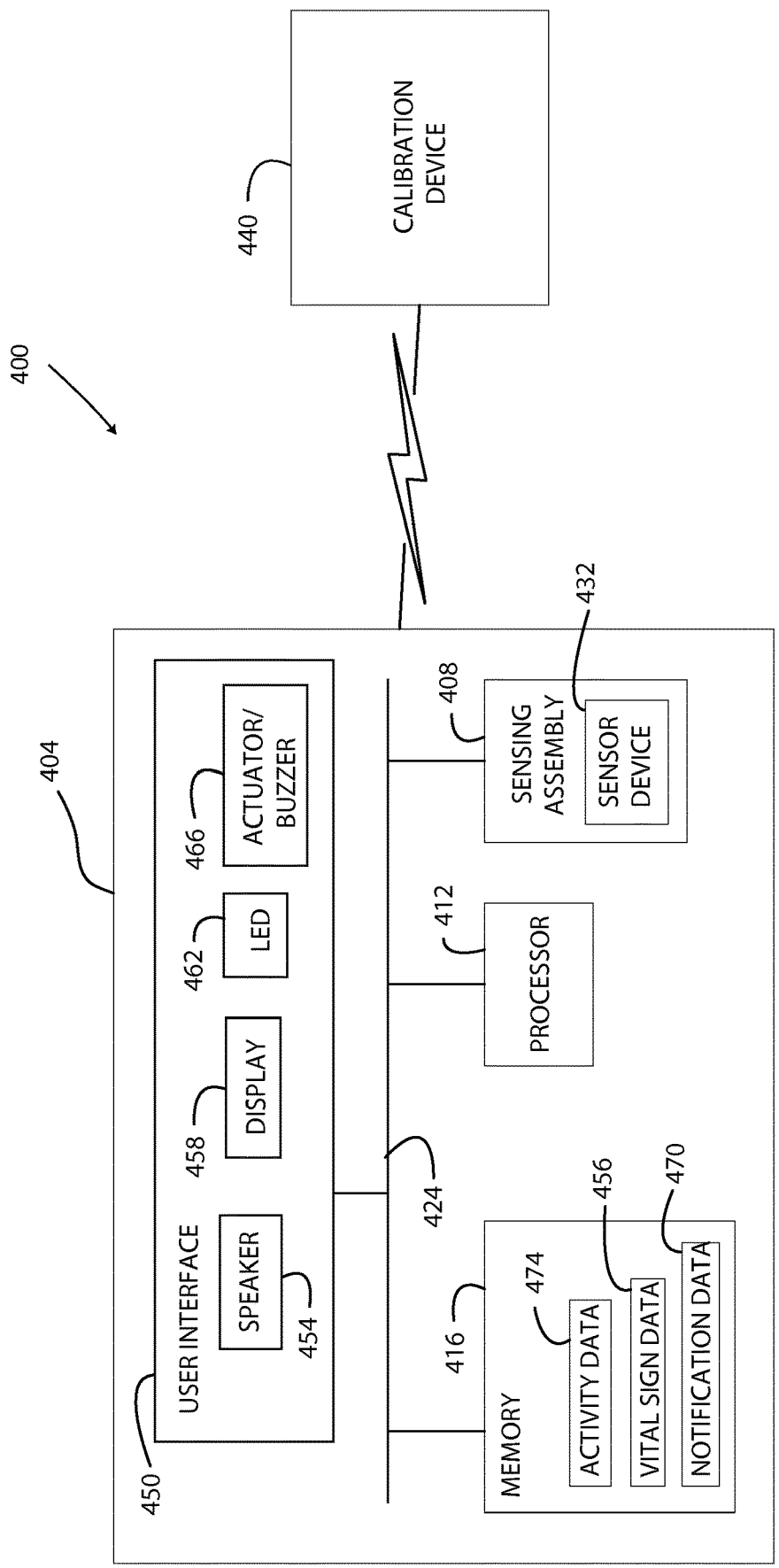
FIG. 5 is a block diagram of another embodiment of a health monitoring system, as disclosed herein, including a body monitoring device and a calibration device.

As shown in FIG. 5, in another embodiment a health monitoring system 400 includes a monitoring device 404 and a calibration device 440. The monitoring device 400 includes a sensor assembly 408, a processor 412, a computer readable memory 416, a sensor device 432, and a user interface 450 each configured for operational connection to a bus 424. The user interface 450 includes a speaker 454, a display screen 458, an LED 462, and a buzzer or actuator 466.

The display screen 458 is configured to display information to the patient 204 or a caretaker. The display screen 458 may display text, numbers, and picture information including video information. The speaker 454 is configured to output audible information, such as a notification, to the user of the monitoring device 404. The LED or LEDs 462 have a corresponding label that conveys information related to a notification to the patient 204 or a caretaker. The actuator 466, in one embodiment, is a vibration unit configured to alert the patient 204 or a caretaker to a notification, for example. The user interface 450 may also include buttons or a microphone configured to receive tactile and audible inputs from the user or patient 204. In some embodiments, the monitoring device 404 does not include the user interface 450, such as in the monitoring device 104.

The monitoring device 404 may receive notification data 470 from the calibration device 440 or another external device over the network 148, such as the server 112, that corresponds to a notification. Notification data 470 may be stored in the memory 416 and may cause audible, visual or tactile feedback to be emitted by the monitoring device 404 to draw the patient's attention. The patient 204 then manually triggers the monitoring device 404 to monitor the motion, position, and/or orientation of the patient 204, for example. If sensor assembly 408 detects the patient 204 is sitting or lying down for instance, the processor 412 is triggered to start a blood pressure estimation and provide context awareness information. The blood pressure estimation once taken is recorded and stored in the memory 416 as the vital sign data 456. In some embodiments, the blood pressure estimation is recorded and stored elsewhere outside the monitoring device 404. If sensor assembly 408 detects the patient 204 is moving, standing, or in motion, then the processor 412 dismisses the notification to measure the blood pressure. In some embodiments, the notification may be displayed or triggered on the user interface 450 of the monitoring device 404 as well as a user interface (not shown) of the calibration device 440 to draw the user's attention. Thus, based on the above, the monitoring device 404, when configured as a blood pressure measuring instrument, measures the patient's blood pressure only when the processor 412 determines that the user is in an appropriate state for the sensing assembly 408 to generate optimized vital sign data 456 that is an accurate representation of the user's blood pressure.

In another example, the monitoring device 404 configured as a blood pressure patch or a blood pressure device, receives notification data 470 from the calibration device 440, the server 144, and/or the network 148. The notification data 470 causes the user interface 450 to issue a human perceptible notification that is indicative of an upcoming measurement event. The notification may be in a form of at least one of a visual, audible, and tactile prompt from the user interface 450. For example, the visual prompt notification may be in a text display format, an alphanumeric display format, a numeric display format, light indication format, an alarm icon, and so forth. The audible prompt notification may be a beeper, a spoken message, a ring tone, and so forth. Tactile prompt notification may be a vibration, a haptic, and so forth.

The notification may be triggered by the patient 204, a stakeholder or a third party such as a doctor, a nurse, a caregiver, or a patient's family. Additionally or alternatively, the notification may be triggered automatically, for example, by another application executing on the monitoring device 404 and/or the calibration device 440. The notification is presented repeatedly at periodic time intervals. For example, the periodic time interval may be set every fifteen minutes during the day and every thirty minutes during the night. In another embodiment, the notification is a time-based reminder, e.g. a particular time or a particular day.

In another embodiment, the sensor assembly 408 of the monitoring device 404 continuously detects daily activities performed by the user 204 and stores activity data 470 corresponding to the detected activities in the memory 416. Once activities are detected, the sensor assembly 414 may transmit the activity data 470 either to the processor 412 for processing or to a database of the memory 416. Any data stored in the database may be processed by the processor 412 or transferred to an external device via the network 148, for example.

Figure 6:
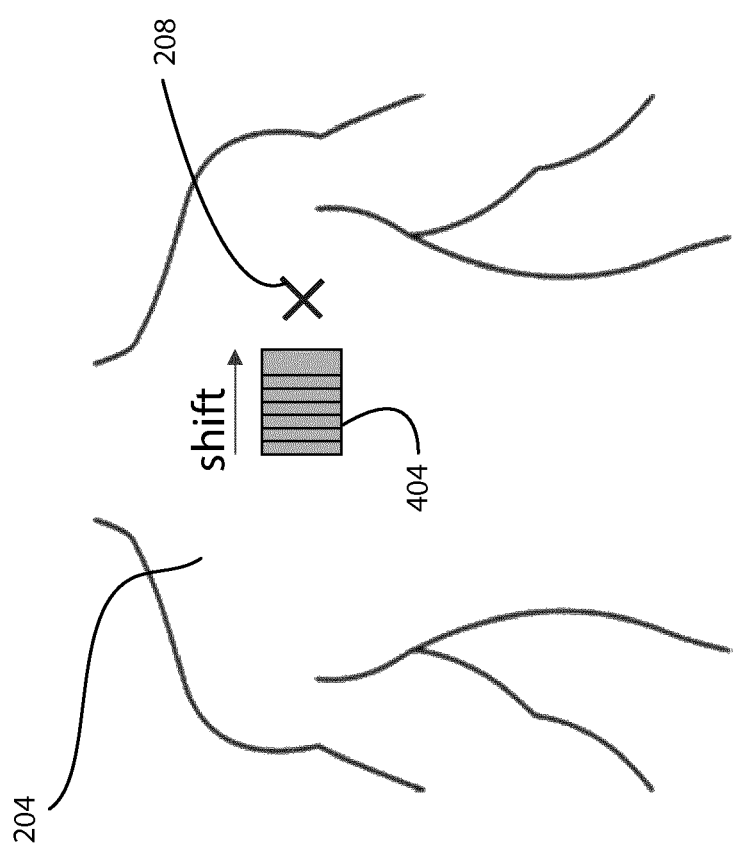
FIG. 6 is a block diagram of the body monitoring device of FIG. 5 applied to a patient.

In FIG. 6, the monitoring device 404 of FIG. 5 is applied to the patient 204 and is spaced apart from the monitoring site 208 in a first position (an initial location). In this embodiment, the proper placement of the monitoring device 404 relative to the monitoring zone 208 is determined by viewing the user interface 450 of the monitoring device 404 while moving the monitoring device 404. To this end, the monitoring device 404 is configured to generate the calibrated data signal and the reposition signal in addition or in alternative to the calibration device 440 generating the calibrated data signal and the reposition signal. For example, the monitoring device 404 is hovered over the patient's body to position the monitoring device 404 to begin detecting the desired vital sign, such as heart rate, EKG, or blood pressure. Once the vital sign is detected, the monitoring device 404 begins to display the signal strength of the vital sign, using the display 458 or the LEDs 462 of the user interface 450, for example. A poor or low signal strength (i.e. the reposition signal) may be displayed with at least one red LED and a good or high-quality signal (i.e. the calibrated data signal) strength may be displayed with at least one green LED of the user interface 450. Moreover, in some embodiments of the monitoring device 404, the light emitted by the LEDs 462 may flash, blink, or others to draw user's attention to indicate the detected signal strength of the desired vital sign. The intensity or blinking rate of the light emitted by the LEDs 462 may vary to covey the signal strength to the user. In another embodiment, the confirmatory signal indicating the signal strength is emitted in the form of audible, visual or tactile prompt by either the user interface 450 or by a user interface (see FIG. 2) of the calibration device 440. The user moves the monitoring device 404 relative to the monitoring zone 208 until an optimal signal strength is obtained as determined by the viewing the user interface 450 of the monitoring device 404.

Figure 7:
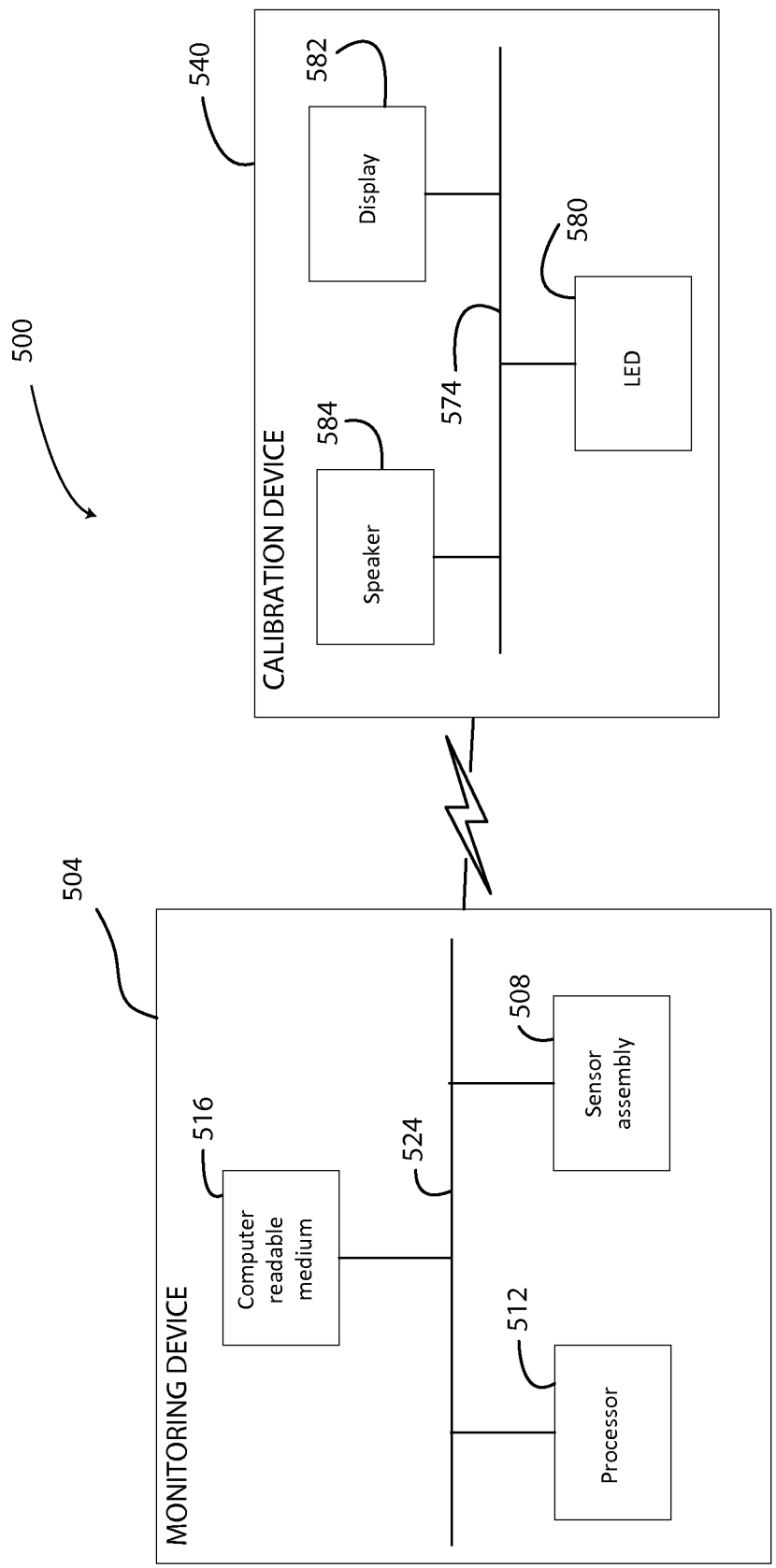
FIG. 7 is a block diagram of another embodiment of a health monitoring system, as disclosed herein, including a body monitoring device and a calibration device.

As shown in FIG. 7, another embodiment of the health monitoring system 500 includes a monitoring device 504 and a calibration device 540. The monitoring device 504 includes a sensor assembly 508, a processor 512, and memory 516 operably connected to each other by way of a bus 524. The calibration device 540 includes an LED 580, a display 582 and a speaker 584 operatively connected to each other by a bus 574. The health monitoring system 500 is configured to implement the method 300 of FIG. 3, for example.

Figure 8:
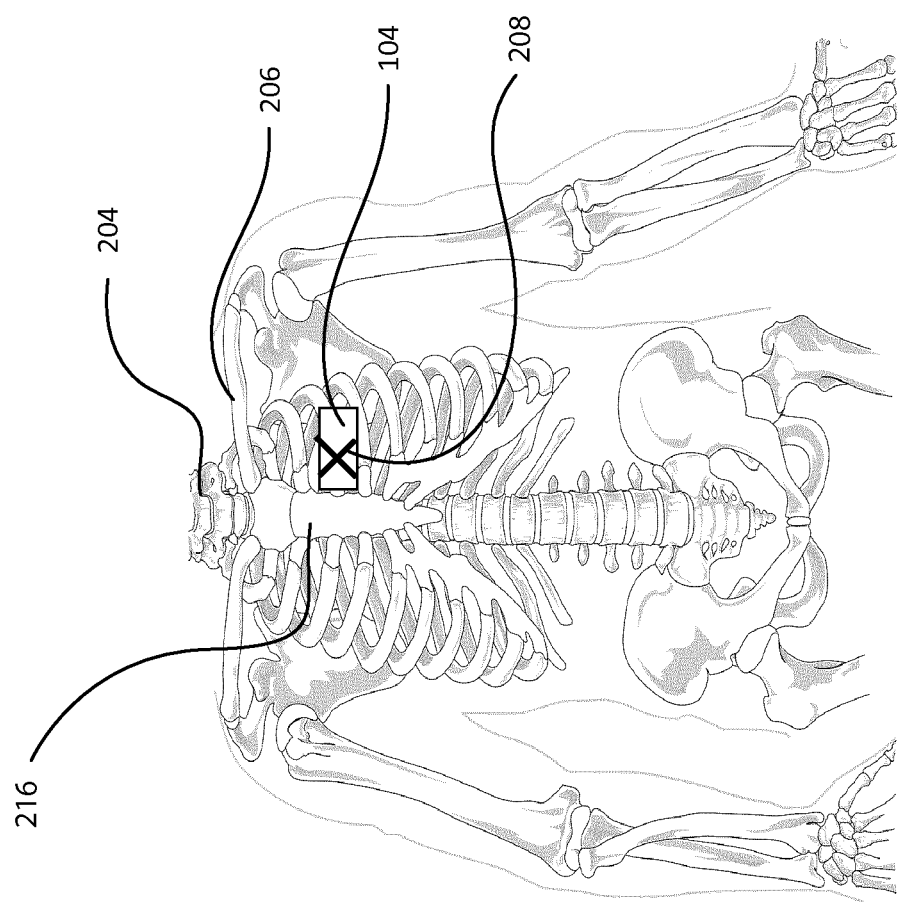
FIG. 8 illustrates a simplified anatomical diagram of an exemplary relative placement and orientation of the monitoring device of FIG. 1.

FIG. 8 illustrates a simplified schematic diagram of a relative placement and orientation of the monitoring device 104 applied to the monitoring zone 208 of the patient 204. A placement of the monitoring device 104, configured as a body monitoring patch, on the patient 204 may be of importance for obtaining high quality data that is optimized for the detection of a particular vital sign. For example, the monitoring device 104 is placed away from and below the center of the left clavicle 206 in a first position. The method of FIG. 3 may be used to properly position the monitoring device 104 over the monitoring zone 208 by optimizing the vital sign data 156 generated by the monitoring device 104.

Figure 9:
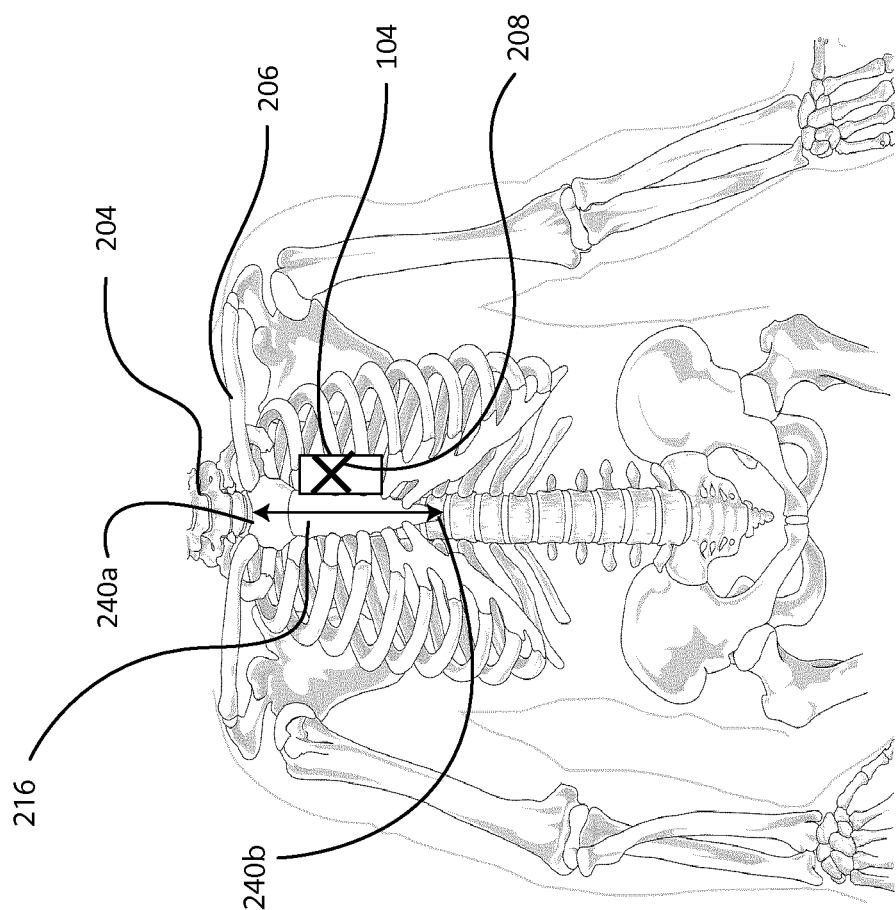
FIG. 9 illustrates a simplified anatomical diagram of another exemplary relative placement and orientation of the monitoring device of FIG. 1.

FIG. 9 illustrates a simplified schematic diagram of a relative placement and orientation of the monitoring device 104 worn by the patient 204. The monitoring device 104 is rotated 90° and is placed below the left clavicle 206 and between top and bottom portions 240a, 240b of the sternum 216. For example, before placement of the monitoring device 104, which is configured as a patch, a distance between the top and bottom portions 240a, 240b of the sternum 216 are determined. Once the distance is determined, the distance is normalized to equal the value one. Next, the monitoring device 104 is placed at a point that is, for example, one-fifth of the normalized distance from the top portion 240a of the sternum 216. This positioning typically corresponds to the monitoring zone 208. After positioning the monitoring device 104 in the rough location described above (i.e. a first position), the method 300 of FIG. 3 is used to "fine-tune" the position of the monitoring device 104 over the monitoring zone 208 by optimizing the vital sign data 156 generated by the monitoring device 104. Depending on the unique physiology of the patient 204, the method 300 may result in the monitoring device 104 being placed on any suitable point from the top portion 240a of the sternum 216 to the bottom portion 240b of the sternum 216 in order to obtain the optimized data.

Figure 10:
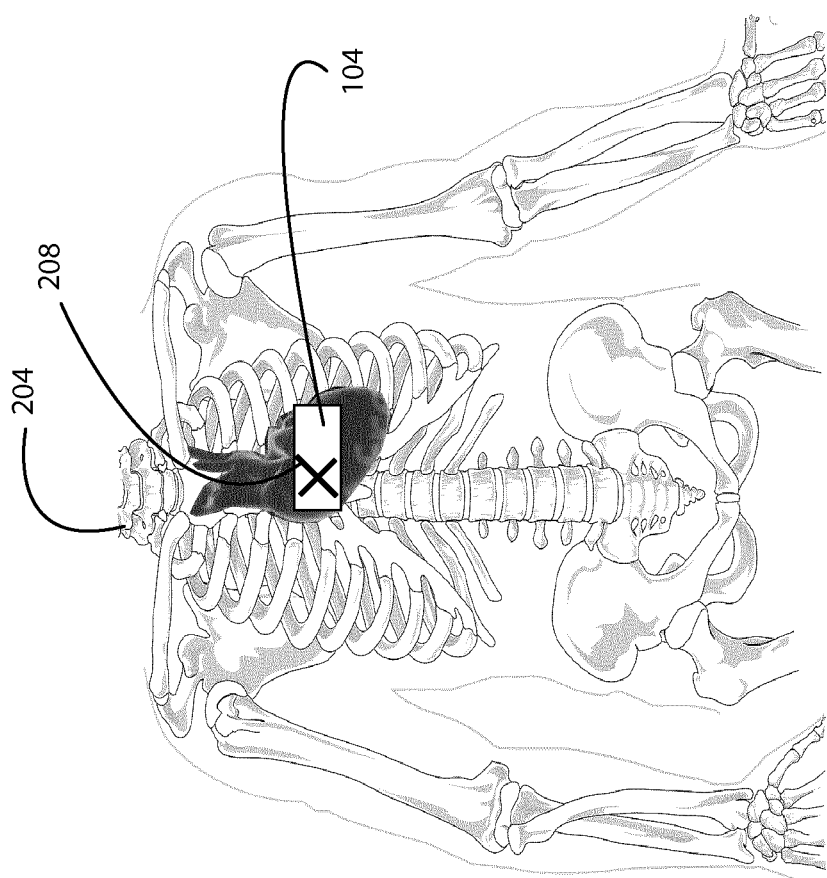
FIG. 10 illustrates another simplified schematic diagram of a relative placement and orientation of the monitoring device of FIG. 1.

FIG. 10 illustrates another simplified schematic diagram of a relative placement and orientation of the monitoring device 104 worn by the patient 204. The monitoring zone 208 and the monitoring device 104 are placed over the heart of the patient 204 where maximum heart beat is typically detected in a first position. The method of FIG. 3 may be used to position properly the monitoring device 104 over the monitoring zone 208 by optimizing the vital sign data 156 generated by the monitoring device 104.

Figure 11:
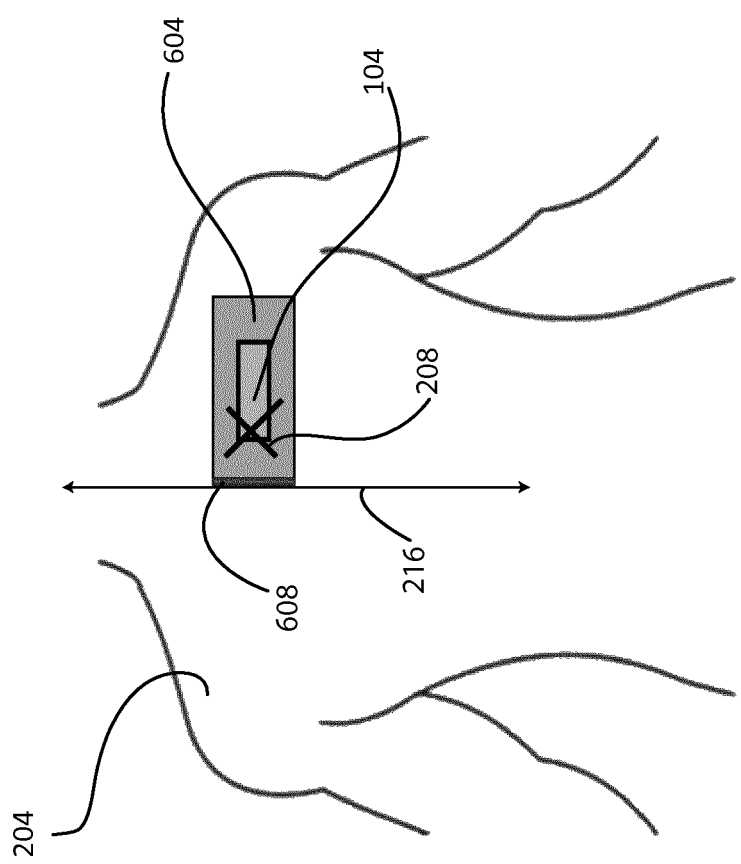
FIG. 11 illustrates a simplified schematic diagram of a relative placement and orientation of the monitoring device of FIG. 1 including a template and an image projector.

FIG. 11 illustrates a simplified schematic diagram of a relative placement and orientation of the monitoring device 104 worn by the patient 204 using a positioning template device 604 that is operatively connected to the monitoring device 104. In this exemplary embodiment, the monitoring device 104 is attached to the template device 604 (also referred to as a sticker or a stencil) that includes a marking 608 to assist the user in placing the monitoring device 104 on the patient 204. The marking 608 is configured to be positioned at an easily identifiable location of the patient's body that results in the monitoring device being positioned at the first position. For example, the template device 604 includes a marking 608 provided as a line that is configured for placement in the middle of the patient's sternum 216. After the user has positioned the template device 604 with the marking 608 aligned with the sternum 216, the adhesive monitoring device 104 is attached, at least temporarily, to the patient 204 and the template device 604 is separated from the monitoring device 104 and removed from the patient 204 leaving behind the monitoring device 104 on the patient 204. After positioning the monitoring device 104 in the first position (i.e. a rough location) provided by the template device 604, the method 300 of FIG. 3 may be used to "fine-tune" the position of the monitoring device 104 over the monitoring zone 208 by optimizing the vital sign data 156 generated by the monitoring device 104.

Figure 12:
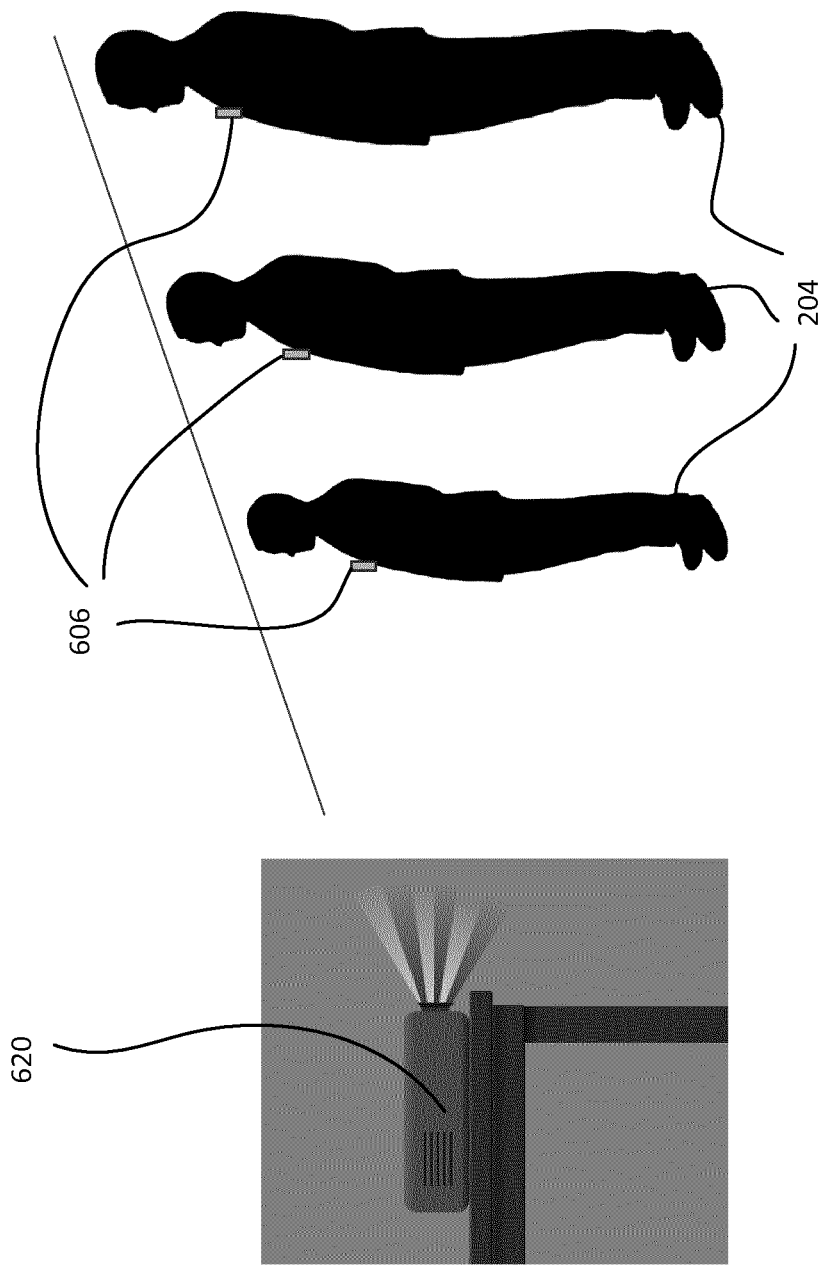
FIG. 12 illustrates a simplified schematic diagram of a projector configured to project a virtual template onto the patient to assist in positioning the monitoring device on the patient, as disclosed herein.

As shown in FIG. 12, in another embodiment, the template is a virtual template 606 that is projected or cast onto the patient 204 with a projector device 620 (or a laser pointer). The virtual template 606 is representative of an initial location (i.e. a first position) of the monitoring device 104. The user positions the monitoring device 104 onto the patient 204 in the position indicated by the virtual template 606. After positioning the monitoring device 104 in the rough location provided by the virtual template 606, the method 300 of FIG. 3 may be used to "fine-tune" the position of the monitoring device 104 over the monitoring zone 208 by optimizing the vital sign data 156 generated by the monitoring device 104.

In FIG. 12, the patient 204 is positioned in front of the projector 620 at position that results in an image being scaled to the same size or height of the patient 204. The image includes the virtual template 606 to indicate the location of the monitoring zone 208 on the patient 204. The monitoring device 104 is then placed on the patient 204 in the location that corresponds to the monitoring zone 208, while the virtual template 606 still being projected. The patient 204 can confirm that the monitoring device 104 is positioned correctly relative to the monitoring zone 208 by viewing the virtual template 606 projected directly onto the positioned monitoring device 104. In some embodiments, a second image may be projected over and overlap a portion of the image of the patient 204 at various distances from the projector 620 using the same projector 620 or a different projector. After positioning the monitoring device 104 in the rough location provided by the projector 620, the method 300 of FIG. 3 may be used to "fine-tune" the position of the monitoring device 104 over the monitoring zone 208 by optimizing the vital sign data 156 generated by the monitoring device 104.

FIGS. 13 and 14 illustrate simplified schematic diagrams of the calibration device 140 configured as a smartphone. The calibration device 140 includes the processor 170 (FIG. 2) having a set of instructions that causes a computer implemented module to superimpose or augment a virtual template 704 for the monitoring device 104 onto a digital representation 708 of the patient 207 (i.e. a selfie or a self-portrait) in the location in which the monitoring device 104 should be positioned (i.e. the first position). In one embodiment, the virtual template 704 is a virtual reality image and/or an augmented reality image of the patient.

In an exemplary operation, the patient 204 points the front-mounted camera 188 of the calibration device 140 at his or her body and an image of the patient 204 is displayed on the display screen 182 as a digital representation 708 in a video or a still picture. The camera 188 generates video data of the patient 204 and the video data is displayed on the display screen 182. Next, the calibration device 140 augments the video data and the image of the patient to include the virtual template 704 overlaid onto the digital representation 708 to identify to the patient 204 the location of the monitoring zone 208 (i.e. the first position). The patient 204, while looking or glancing at the display screen 182, then positions the monitoring device 104 on his or her body in the location identified by the virtual template 704. If the monitoring device 104 is misplaced and the misplaced location is captured by the camera 188, the calibration device 140 may alert the user of the misplacement with either a visual or audible alert message via the user interface 168. After positioning the monitoring device 104 in the rough location provided by the augmented reality screen of the calibration device 140, the method 300 of FIG. 3 may be used to "fine-tune" the position of the monitoring device 104 over the monitoring zone 208 by optimizing the vital sign data 156 generated by the monitoring device 104.

Figure 15:
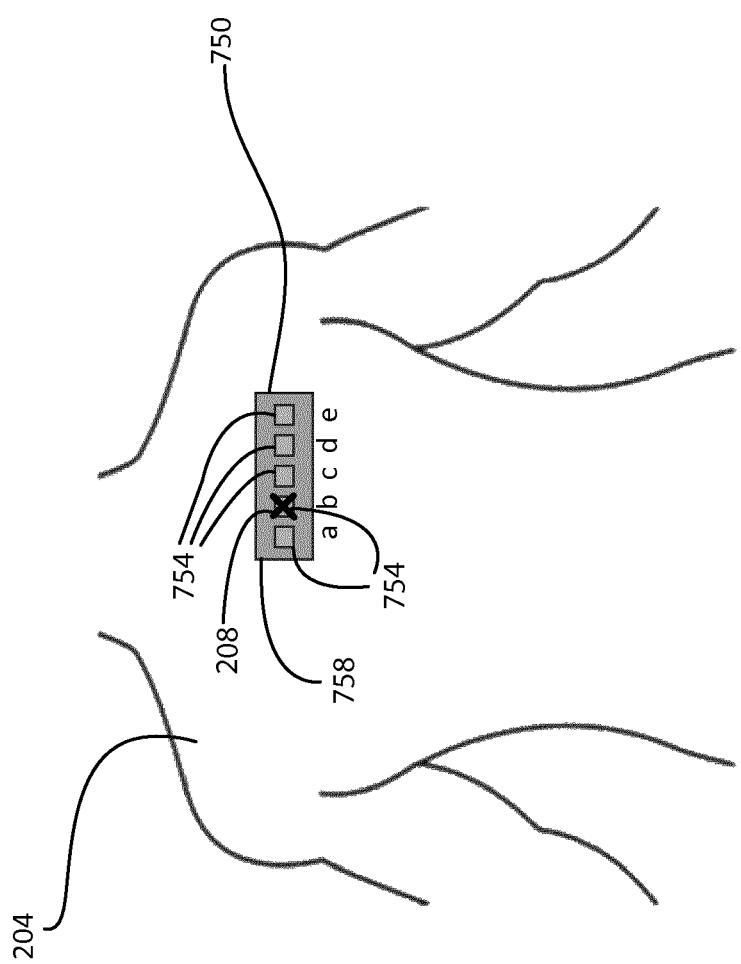
FIG. 15 illustrates a simplified schematic diagram of another embodiment of a monitoring device, as disclosed herein.

FIG. 15 illustrates another embodiment of a monitoring device 750 which is provided as a patch and comprises an array of sensor elements 754 encapsulated in a patch housing 758. The patch housing 758 may include a single row of the sensor elements 754 or a plurality of rows and columns of the sensor elements 754.

In operation, the monitoring device 750 is positioned on the patient 204 in a location corresponding to the monitored zone 208. Next, each of the sensor elements 754 sends a signal to the calibration device 140 either individually or substantially simultaneously. The calibration device 140 identifies the sensor element 754 having the best signal strength and/or the most optimized data to monitor the selected vital sign and to generate the vital sign data 156. Typically, the other sensor elements 754 are not used to monitor the vital sign. In other embodiments, more than one of the sensor elements 754 is used to monitor the vital sign. A first sensor element 754 may monitor a first vital sign, and a second sensor element 754 may monitor a second vital sign.

In the example of FIG. 15, the calibration device 104 determines that the senor device 754 in row B is closest to the monitored zone 208 and generates the most optimized data, and the monitoring device 750 configures the sensor device 754 in row B to generate the vital sign data 156.

A software application ("app") such as a mobile app, an electronic app, or any suitable app comprises of a set of instructions regarding a relative placement, orientation, or the like of the monitoring device may be loaded or installed on any device. The instructions of the relative placement of the monitoring device described above have been shown by way of example and can be in the form of any suitable visual and audible signs. The instructions are an autonomous electronic assistant. Warnings such as placement error, translational error, rotational error, or the like can be presented in the form of visual, audible, and tactile feedback to draw the user attention.

The embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling with the spirits and scope of this disclosure.

Embodiments within the scope of the disclosure may also include non-transitory computer-readable storage media or machine-readable medium for carrying or having computer-executable instructions or data structures stored thereon. Such non-transitory computer-readable storage media or machine-readable medium may be any available media that can be accessed by a general purpose or special purpose computer. By way of example, and not limitation, such non-transitory computer-readable storage media or machine-readable medium can comprise of RAM, ROM, EEPROM, CD-ROM or other optical disk storage, magnetic disk storage or other magnetic storage devices, or any other medium which can be used to carry or store desired program code means in the form of computer-executable instructions or data structures. Combinations of the above should also be included within the scope of the non-transitory computer-readable storage media or machine-readable medium.

Embodiments may also be practiced in distributed computing environments where tasks are performed by local and remote processing devices that are linked (either by hardwired links, wireless links, or by a combination thereof) through a communications network.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

While the invention has been described with reference to various embodiments, it will be understood that these embodiments are illustrative and that the scope of the disclosure is not limited to them. Many variations, modifications, additions, and improvements are possible. More generally, embodiments in accordance with the invention have been described in the context or particular embodiments. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A method of calibrating a monitoring device to generate calibrated vital sign data using a calibration device, the method comprising:
    projecting a virtual template onto a patient, the virtual template identifying a location of a first position on the patient;
    positioning the monitoring device in the first position on the patient based on the projection of the virtual template;
    generating vital sign data with a sensing assembly of the positioned monitoring device;
    processing the vital sign data with the calibration device to determine if the vital sign data is calibrated vital sign data or uncalibrated vital sign data;
    generating a calibrated data signal if the vital sign data is calibrated vital sign data;
    generating a reposition signal if the vital sign data is uncalibrated vital sign data; and
    repositioning the monitoring device on the patient until the calibrated data signal is generated.

2. The method of claim 1, further comprising:
    transmitting the vital sign data from the positioned monitoring device to the calibration device.

3. The method of claim 1, further comprising:
    generating the calibrated data signal with the calibration device; and
    generating the reposition signal with the calibration device.

4. The method of claim 1, further comprising:
    generating the calibrated data signal with the monitoring device; and
    generating the reposition signal with the monitoring device.

5. The method of claim 4, further comprising:
    displaying the calibrated data signal with a user interface of the monitoring device; and
    displaying the reposition signal with the user interface of the monitoring device.

6. The method of claim 1, further comprising:
    using a template device connected to the monitoring device to position the monitoring device in the first position; and
    removing the template device from the positioned monitoring device prior to generating the vital sign data.

7. The method of claim 1, wherein the calibrated data signal is generated based on a comparison of a signal strength of the vital sign data to a signal strength threshold.

8. The method of claim 1, wherein the calibrated data signal is generated based on a comparison of a value of the vital sign data to a data range.

9. A method of calibrating a monitoring device to generate calibrated vital sign data using a calibration device, the method comprising:
    displaying an image of a patient on a display screen of the calibration device;
    augmenting the image to include a virtual template identifying a location of a position on the patient;
    positioning the monitoring device in the position on the patient based on the virtual template;
    generating vital sign data with a sensing assembly of the positioned monitoring device;
    processing the vital sign data with the calibration device to determine if the vital sign data is calibrated vital sign data or uncalibrated vital sign data;
    generating a calibrated data signal if the vital sign data is calibrated vital sign data;
    generating a reposition signal if the vital sign data is uncalibrated vital sign data; and
    repositioning the monitoring device on the patient until the calibrated data signal is generated.

10. A health monitoring system, comprising:
    a monitoring device including a sensing assembly configured to generate vital sign data of a patient;
    a calibration device operably connected to the monitoring device and including a processor configured to calibrate the monitoring device by:
        generating a calibrated data signal if the vital sign data is calibrated vital sign data, and
        generating a reposition signal if the vital sign data is uncalibrated vital sign data; and
    a template device operably connected to the monitoring device, the template device including a marking configured to be positioned at a location of the patient's body that results in the monitoring device being positioned at a first position on the patient,
    wherein the monitoring device is configured to be moved on the patient from the first position to a second position in response to the calibration device generating the reposition signal, and
    wherein the template device is separated from the monitoring device after the monitoring device is positioned at the first position and prior to the generation of the vital sign data.

11. The health monitoring system of claim 10, wherein the monitoring device further comprises:
    a memory configured to store the vital sign data; and
    a user interface configured to display the reposition signal and the calibrated data signal generated by the calibration device.

12. The health monitoring system of claim 10, further comprising:
    a projector device configured to project an image of a virtual template onto the patient,
    wherein the virtual template is representative of the location of the first position of the monitoring device.

13. The health monitoring system of claim 10, wherein the calibration device further comprises:
    a camera configured to generate video data of the patient; and
    a display screen configured to display the video data, wherein the processor of the calibration device is further configured to augment the video data to include a virtual template located on the patient at the first position to assist the patient in positioning the monitoring device at the first position.

* * * * *